(12) United States Patent
Lu et al.

(10) Patent No.: US 7,938,538 B2
(45) Date of Patent: May 10, 2011

(54) METHODS AND DEVICES FOR RAPID MEASUREMENT OF VISUAL SENSITIVITY

(75) Inventors: Zhong-Lin Lu, Irvine, CA (US); Luis A. Lesmes, LaJolla, CA (US)

(73) Assignee: University of Southern California, Los Angeles, CA (US)

( * ) Notice: Subject to any disclaimer, the term of this patent is extended or adjusted under 35 U.S.C. 154(b) by 26 days.

(21) Appl. No.: 12/463,901

(22) Filed: May 11, 2009

(65) Prior Publication Data
US 2010/0007851 A1 Jan. 14, 2010

Related U.S. Application Data

(60) Provisional application No. 61/052,142, filed on May 9, 2008.

(51) Int. Cl.
*A61B 3/02* (2006.01)

(52) U.S. Cl. .......... 351/222; 351/237; 351/239
(58) Field of Classification Search .......... 351/222, 351/223, 237, 238, 239, 242, 243
See application file for complete search history.

(56) References Cited

U.S. PATENT DOCUMENTS

| | | | |
|---|---|---|---|
| 7,354,155 B2 * | 4/2008 | Holladay | 351/239 |
| 7,427,138 B2 * | 9/2008 | Ellenbogen | 351/243 |
| 2007/0052927 A1 * | 3/2007 | Noda et al. | 351/239 |

* cited by examiner

*Primary Examiner* — Huy K Mai
(74) *Attorney, Agent, or Firm* — DLA Piper LLP (US)

(57) ABSTRACT

The present invention relates to methods for efficient adaptive measurement and classification of contrast sensitivity functions and spatiotemporal contrast sensitivity surface by selecting the most informative stimulus before each trial. Also disclosed are devices for implementing such methods.

26 Claims, 12 Drawing Sheets

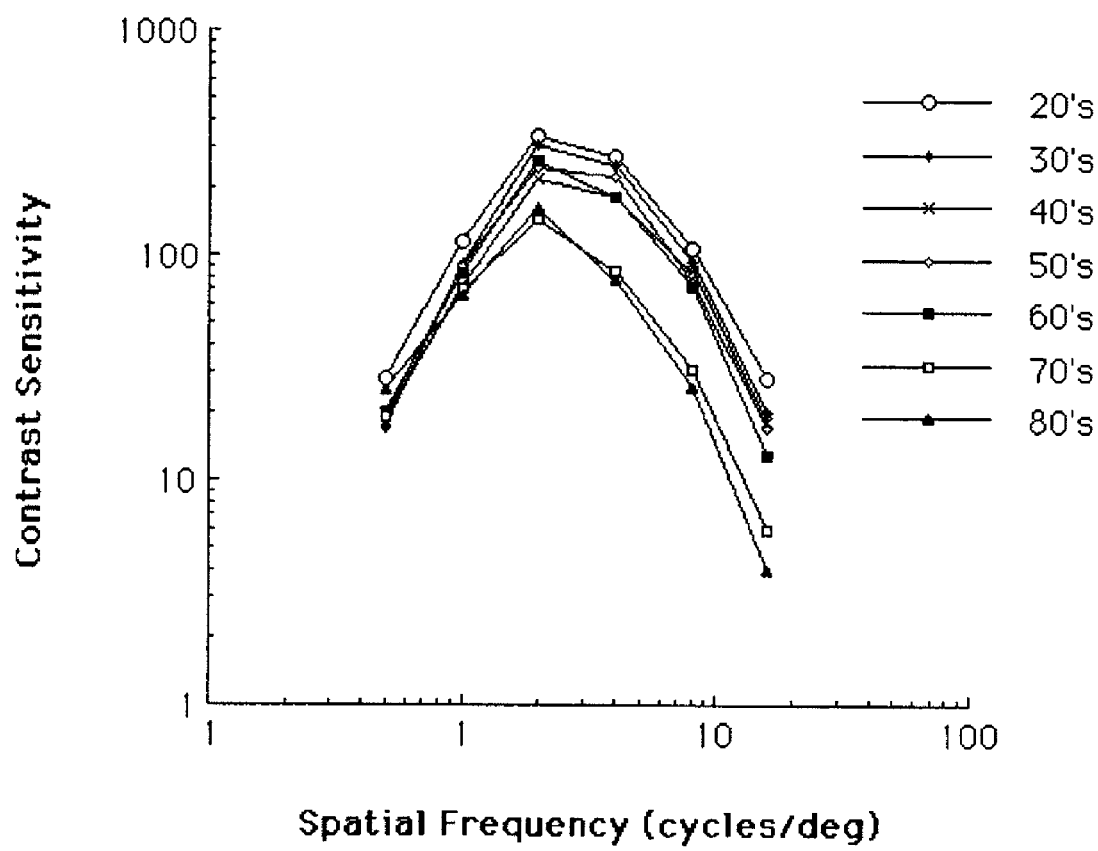
Figure 1 Contrast sensitivity functions of seven age groups
(Prior Art)

METHODS AND DEVICES FOR RAPID MEASUREMENT OF VISUAL SENSITIVITY

RELATED APPLICATION

The present application claims priority to U.S. Provisional Application Ser. No. 61/052,142, filed on May 9, 2008, the content of which is incorporated herein by reference in its entirety.

FUNDING

This invention was made with support in part by grants from NEI through a UCI subcontract (RO1 EY017491-05) and NIH (F32EY016660, EY017491, and EY-007605). Therefore, the U.S. government has certain rights.

FIELD OF THE INVENTION

The present invention relates in general to visual sensitivity. More specifically, the invention provides methods and devices for rapid measurement of contrast sensitivity function (CSF) and spatiotemporal contrast sensitivity surface (CSS).

BACKGROUND OF THE INVENTION

The spatial resolution of the visual system is usually assessed using a simple measure of static visual acuity. A typical visual acuity test consists of a number of high contrast, black-on-white targets of progressively smaller size. The smallest target that one can successfully read denotes one's visual acuity. For example, if the smallest letters that you can read upon a Snellen Eye Chart subtend 5 minutes of arc (minarc) in height, you are said to have 20/20 (or "normal") acuity. That is, the smallest letter that your visual system can successfully resolve is 5 minarc in height.

Visual acuity is a common measure of visual status because (1) it is easy to measure and (2) small amounts of refractive error in the eye yield marked declines in acuity test performance. Fortunately, most sources of refractive error are correctable via glasses or contact lenses.

However, recent findings have demonstrated that visual spatial processing is organized as a series of parallel—but independent—channels in the nervous system; each "tuned" to targets of a different size. As a result of this parallel organization of the visual nervous system, visual acuity measurements no longer appear to adequately describe the spatial visual abilities of a given individual. Modern vision research has clearly demonstrated that the capacity to detect and identify spatial form varies widely as a function of target size, contrast, and spatial orientation (see Braddick, Campbell & Atkinson, 1978, *Handbook of sensory physiology* or Olzak & Thomas, 1981, Journal of Optical Society of America, 71(1): 64-70; Graham, 1989, *Visual pattern analyzers*. Oxford University Press, USA; De Valois & De Valois, 1988, Spatial Vision. New York: Oxford.). As a consequence, a simple assessment of visual acuity often does not predict an individual's ability to detect objects of larger size (Faye, 2005, Contrast sensitivity tests in predicting visual function. *International Congress Series Vision* 2005—*Proceedings of the International Congress held between 4 and 7 Apr. 2005 in London, UK,* 1282, 521-524; Ginsburg, Evans, Sekuler & Harp, 1983, Investigative Opthalmology & Visual Science, 24, p. 798-802; Ginsburg, 1984, A new contrast sensitivity vision test chart. *American journal of optometry and physiological optics,* 61(6), 403; Ginsburg, 2006, Current Opinion in Opthalmology, 17(1):19-26; Watson, Barlow & Robson, 1983, Nature, 302(5907):419-22).

Contrast sensitivity testing complements and extends the assessment of visual function provided by simple acuity tests. At the cost of more complex and time-consuming procedures, contrast sensitivity measurements yield information about an individual's ability to see low-contrast targets over an extended range of target size (and orientation).

Contrast sensitivity tests use sine-wave gratings as targets instead of the letter optotypes typically used in tests of acuity. Sine-wave gratings possess useful mathematical properties and researchers have discovered that early stages of visual processing are optimally "tuned" to such targets (Campbell & Robson, 1968, Application of Fourier analysis to the visibility of gratings. *J Physiol,* 197(3), 551-66; De Valois & De Valois, 1988, Spatial Vision. New York: Oxford; Watson et al., 1983, Nature, 302(5907):419-22).

A contrast sensitivity assessment procedure consists of presenting the observer with a sine-wave grating target of a given spatial frequency (i.e., the number of sinusoidal luminance cycles per degree of visual angle). The contrast of the target grating is then varied while the observer's contrast detection threshold is determined. Typically, contrast thresholds of this sort are collected using vertically oriented sine-wave gratings varying in spatial frequency from 0.5 (very wide) to 32 (very narrow) cycles per degree of visual angle.

Because high levels of visual sensitivity for spatial form are associated with low contrast thresholds, a reciprocal measure (1/threshold) termed the contrast sensitivity score is computed. The contrast sensitivity scores obtained for each of the sine-wave gratings examined are then plotted as a function of target spatial frequency yielding the contrast sensitivity function (CSF). Some typical CSF's are depicted in FIG. 1. Note the characteristic inverted-U shape of the CSF and its logarithmic axes.

SUMMARY OF THE INVENTION

The present invention relates to novel methods and devices for efficient adaptive measurement and classification of contrast sensitivity functions and spatiotemporal contrast sensitivity surface by selecting the most informative stimulus before each trial.

Accordingly, in one aspect, the invention features a quick contrast sensitivity function (qCSF) method. The method comprises (a) providing a prior probability density, $p(\theta)$, (b) selecting a grating stimulus, s, that minimizes the expected entropy of the Bayesian posterior, (c) displaying s to a subject, (d) receiving a response to s from the subject, (e) updating the prior probability density $p(\theta)$ according to the Bayes rule and the response received in step (d), (f) reiterating steps (b) through (e), and (g) terminating the process according to a stopping criterion. The method may further comprise a step of determining whether the vision of the subject is abnormal.

In another aspect, the invention features a device for visual examination, comprising: (a) computation means for providing a prior probability density, $p(\theta)$, selecting a grating stimulus, s, that minimizes the expected entropy of the Bayesian posterior, updating the prior $p(\theta)$ according to the Bayes rule and a response to s by a subject to which s is displayed, and terminating a visual examination according to a stopping criterion; (b) display means coupled to the computation means and displaying s to the subject; and (c) recording means for receiving the response to s by the subject and transmitting it to the computation means. The device may further comprise diagnostic means for determining whether the vision of the subject is abnormal.

$p(\theta)$ is defined over (1) peak sensitivity, $\gamma_{max}$, (2) peak spatial frequency, $f_{max}$, (3) bandwidth at half-peak sensitivity, $\beta$, and (4) low spatial frequency truncation, $\delta$.

Also within the invention is a method for classifying CSFs. The method comprises (a) providing a prior probability of class membership, (b) selecting a grating stimulus, s, that minimizes the expected entropy of the Bayesian posterior, (c) displaying s to a subject, (d) receiving a response to s from the subject, (e) updating the prior probability of class membership according to the Bayes rule and the response received in step (d), (f) reiterating steps (b) through (e), and (g) terminating the process according to a stopping criterion. The method may further comprise a step of determining the pathologic class of the vision of the subject if the vision of the subject is abnormal.

In addition, the invention features a device for visual examination, comprising: (a) computation means for providing a prior probability of class membership, selecting a grating stimulus, s, that minimizes the expected entropy of the Bayesian posterior, updating the prior probability of class membership according to the Bayes rule and a response to s by a subject to which s is displayed, and terminating a visual examination according to a stopping criterion; (b) display means coupled to the computation means for receiving s from the computation means and displaying s to the subject; and (c) recording means for receiving the response to s by the subject and transmitting it to the computation means. The device may further comprise diagnostic means for determining the pathologic class of the vision of the subject if the vision of the subject is abnormal.

In the methods and devices described above, s may be defined by spatial frequency and contrast. The stopping criterion may be a predetermined number of trials.

Moreover, the invention provides a method for rapid measurement of spatiotemporal contrast sensitivity surface (CSS). The method comprises (a) providing prior spatial CSFs at predetermined temporal frequencies, temporal CSFs at predetermined spatial frequencies, and CSFs at co-varied spatial and temporal frequencies and predetermined constant speeds, (b) selecting a grating stimulus, s, that maximizes the expected information gain from the Bayesian posteriors, (c) displaying s to a subject, (d) receiving a response to s from the subject, (e) updating the prior CSFs according to the Bayes rule and the response received in step (d), (f) reiterating steps (b) through (e), and (g) terminating the process according to a stopping criterion. The method may further comprise a step of determining whether the vision of the subject is abnormal.

The invention further provides a device for visual examination, comprising: (a) computation means for providing prior spatial CSFs at predetermined temporal frequencies, temporal CSFs at predetermined spatial frequencies, and CSFs at co-varied spatial and temporal frequencies and predetermined constant speeds, selecting a grating stimulus, s, that maximizes the expected information gain from the Bayesian posteriors, updating the prior CSFs according to the Bayes rule and a response to s by a subject to which s is displayed, and terminating a visual examination according to a stopping criterion; (b) display means coupled to the computation means for receiving s from the computation means and displaying s to the subject; and (c) recording means for receiving the response to s by the subject and transmitting it to the computation means. The device may further comprise diagnostic means for determining whether the vision of the subject is abnormal.

In the method and device described above, grating stimulus s may be defined by spatial and temporal frequencies and contrast. The stopping criterion may be a predetermined number of trials.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

BRIEF DESCRIPTION OF THE FIGURES

FIG. 1. Contrast sensitivity functions of seven age groups (Prior Art).

FIG. 2. The quick spatial CSF method. The upper panel

DETAILED DESCRIPTION OF THE INVENTION

One object of the invention is to provide adaptive testing methods that (1) estimate CSFs with the precision of psychophysical testing and short testing time of cards/charts, and (2) classify CSFs into pathological categories based on candidate CSFs with very short test time.

Accordingly, the invention provides a quick contrast sensitivity function (qCSF) method. The method involves the steps of (a) providing a prior probability density, $p(\theta)$, (b) selecting a grating stimulus, s, that minimizes the expected entropy of the Bayesian posterior, (c) displaying s to a subject, (d) receiving a response to s from the subject, (e) updating the prior $p(\theta)$ according to the Bayes rule and the response received in step (d), (f) reiterating steps (b) through (e), and (g) terminating the process according to a stopping criterion.

Figure 13:
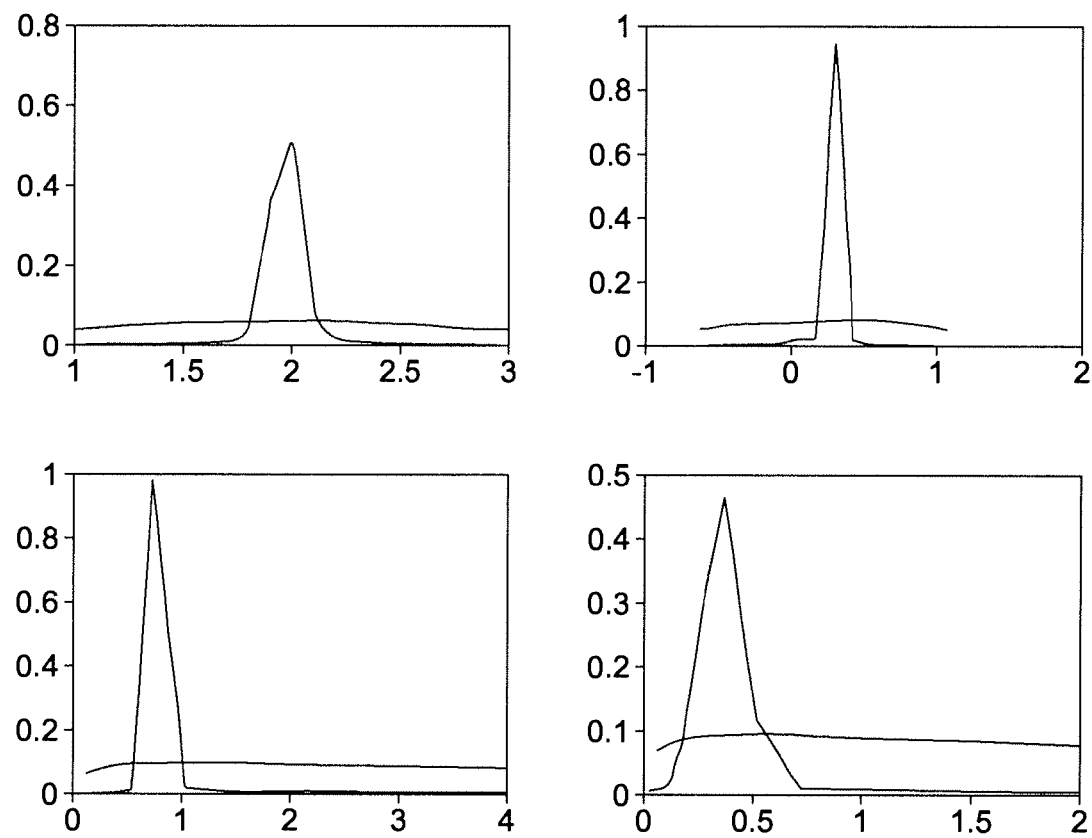
FIG. 13. The priors and posterior densities for the CSF parameters, obtained from a single qCSF session.

For the qCSF, it's necessary to first define a discrete, gridded parameter space, $T_\theta$, that consists of four-dimensional vectors $\theta=(f_{max},\gamma_{max},\beta,\delta)$, which represent the full range of CSFs that potentially characterize the test observer. At the beginning of the method, a prior probability density, $p(\theta)$, which reflects baseline knowledge about the observer's CSF, is defined over the space, $T_\theta$. The prior can be informed by knowledge about the task or the test population. For example, although the gain and frequency of the CSF's peak can vary greatly across subjects, there is less variability in its bandwidth. FIG. 13 presents some examples of the priors (defined by hyperbolic secant functions; King-Smith et al., 1997) for each of the four CSF parameters.

Describing the CSF with a simple functional form, the qCSF method searches one-step-ahead for the stimulus contrast and spatial frequency minimizing the expected entropy of the posterior jointly defined over four parameters: (1) peak sensitivity, (2) peak spatial frequency, (3) bandwidth at half-peak sensitivity, and (4) low spatial frequency truncation. Typically, less than 10 trials are sufficient for detecting abnormal CSFs. A "trial" refers to the presentation of a stimulus to a subject and the response of the subject to the stimulus.

In qCSF, a Bayesian prior is defined over a four-dimensional gridded space of CSF parameters. Following each trial, the prior is updated via Bayes' rule, based on the subject's response to the presented grating stimulus. Before each trial, the grating stimulus is determined by a one-step-ahead search over the space of possible stimuli jointly defined by grating frequency and grating contrast. The presented stimulus is one that minimizes the expected entropy of the Bayesian posterior or maximizes the expected information gain. The pre- and post-trial calculations can be implemented as described in Appendix A in Example III below, or by any other method known in the art.

qCSF can be used to determining whether the vision of a subject is abnormal, e.g., by distinguishing normal and abnormal CSFs. Thus, qCSF has a great value for detecting visual pathology and tracking its progression or remediation.

The invention also provides a method for classifying CSFs. The method involves the steps of (a) providing a prior probability of class membership, (b) selecting a grating stimulus, s, that minimizes the expected entropy of the Bayesian posterior, (c) displaying s to a subject, (d) receiving a response to s from the subject, (e) updating the prior probability of class membership according to the Bayes rule and the response received in step (d), (f) reiterating steps (b) through (e), and (g) terminating the process according to a stopping criterion. The method may further comprise a step of determining the pathologic class of the vision of the subject if the vision of the subject is abnormal.

The empirical measure (information) used by the quick CSF method can also be used to classify subjects based on candidate classes for normal and abnormal vision (Cobo-Lewis, 1997) and also to combine the results of multiple, concurrent qCSF methods applied to different but complementary stimulus conditions. For CSF classification, classes are defined based on historical measurement of normal and abnormal contrast sensitivity functions.

For CSF classification, the prior probability $p(c(i))$, i=1, 2, . . . n, is defined over some number of classes, $c(i)$. Before the test starts, the prior probability of class membership can depend on structural testing of the retina, or the results of previous behavioral testing. Before each trial, the expected entropy change is calculated as a function of different possible stimuli, and the stimulus chosen is that which most minimizes the uncertainty (entropy) of class membership (Cobo-Lewis, 1997) or maximizes the expected information gain. Typically, 10-20 or 20-30 trials are sufficient for classifying abnormal CSFs.

The invention further provides a method for rapid measurement of spatiotemporal contrast sensitivity surface (CSS). The method involves the steps of (a) providing prior spatial CSFs at predetermined temporal frequencies, temporal CSFs at predetermined spatial frequencies, and CSFs at co-varied spatial and temporal frequencies and predetermined constant speeds, (b) selecting a grating stimulus, s, that maximizes the expected information gain from the Bayesian posteriors, (c) displaying s to a subject, (d) receiving a response to s from the subject, (e) updating the prior CSFs according to the Bayes rule and the response received in step (d), (f) reiterating steps (b) through (e), and (g) terminating the process according to a stopping criterion.

The spatiotemporal contrast sensitivity surface (CSS) reflects how contrast sensitivity over 2-D stimulus space of spatial and temporal frequency. The invention provides a procedure (quick Surface or qSurface) for improving the measurement of the two-dimensional surface that represents the spatio-temporal contrast sensitivity function. This surface can be estimated via cross-sections which are individual spatial and temporal contrast sensitivity functions, as well as constant speed CSFs at co-varied spatial and temporal frequencies. Because of the great amount of data collection needed, the measurement of a spatial contrast sensitivity function is often performed at a fixed temporal frequency, and temporal contrast sensitivity functions are measured at fixed spatial frequencies. Therefore, the entire surface is estimated by combining qCSF applications dedicated to measuring different spatial and temporal sensitivity functions simultaneously. The qSurface procedure provides the means to combine several dozen qCSF methods at once. Before each trial, the pre-trial evaluation of many different qCSF procedures is performed. For each possible stimulus, the total information that each stimulus provides about all the CSF cross-sections that pass through it is calculated. The stimulus chosen for the next trial is the one that maximizes the information gained about the orthogonal or diagonal contrast sensitivity cross-sections through the spatio-temporal contrast sensitivity surface. After each trial, the Bayesian posteriors defined over all the surface's cross-sections are updated. Typically, 300-500 trials are sufficient for accurate CSS estimates.

The qSurface priors are chosen in similar ways as in qCSF described herein. The priors of the present invention can also be set based on the results from the literature. The latter method would further improve the efficiency of the procedure.

In addition, the invention provides devices for implementing the methods of the invention. Generally, a device of the invention includes computation means (e.g., a computer) with various capabilities. The device also includes display means (e.g., a monitor) coupled to the computation means for receiving s from the computation means and displaying s to the subject. Another part of the device is recording means (e.g., a switch) for receiving the response to s by the subject and transmitting it to the computation means.

In one embodiment, the computation means can (a) provide a prior probability density, $p(\theta)$, (b) select a grating stimulus, s, that minimizes the expected entropy of the Bayesian posterior, and (c) update the prior $p(\theta)$ according to the Bayes rule and a response to s by a subject to which s is displayed. In another embodiment, the computation means can (a) provide a prior probability of class membership, (b) select a grating stimulus, s, that minimizes the expected entropy of the Bayesian posterior, and (c) update the prior probability of class membership according to the Bayes rule and a response to s by a subject to which s is displayed. In still another embodiment, the computation means can (a) provide prior spatial CSFs at predetermined temporal frequencies, temporal CSFs at predetermined spatial frequencies, and CSFs at co-varied spatial and temporal frequencies and predetermined constant speeds, (b) select a grating stimulus, s, that maximizes the expected information gain from the Bayesian posteriors, and (c) update the prior CSFs according to the Bayes rule and a response to s by a subject to which s is displayed. The computation means can also terminate a visual examination according to a stopping criterion (e.g., a predetermined number of trials).

For diagnostic purposes, a device of the invention may further include diagnostic means (e.g., as a part of the computer) for determining whether the vision of the subject is abnormal or the pathologic class of the vision of the subject if the vision of the subject is abnormal.

Moreover, the invention provides software programs for implementing the methods of the invention, as well as computer-readable media containing instructions for performing the methods of the invention.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

Example I

Efficient Adaptive Measurement and Classification of Contrast Sensitivity Functions Purpose. The contrast sensitivity function (CSF), describing observer's grating sensitivity as a function of spatial frequency[1], is a canonical measure of spatial vision. Clinically, a number of visual neuro-pathologies exhibit characteristic CSF deficits[2]. The cards/charts currently used for clinical testing, though easy to use, limit the sampling range and grain of grating contrast and spatial frequency, and therefore limit test precision. We sought to develop adaptive testing methods that (1) estimate CSFs with the precision of psychophysical testing and short testing time of cards/charts, and (2) classify CSFs into pathological categories based on candidate CSFs with very short test time.

Method. Describing the CSF with a simple functional form, the quick CSF (qCSF) method searches one-step-ahead for the stimulus contrast and spatial frequency minimizing the expected entropy[3-5] of the posterior jointly defined over four parameters: (1) peak sensitivity, (2) peak spatial frequency, (3) bandwidth at half-peak sensitivity, and (4) low spatial frequency truncation. In an orientation discrimination task, observers ran the qCSF concurrently with an adaptive method estimating thresholds independently at 6 spatial frequencies. Each of four sessions provided two qCSF estimates and one conventional CSF estimate. For adaptive classification, candidates included one normal CSF, one CSF with general-deficit, and three CSFs with low, middle and high frequency-specific deficits. Stimulus placement minimized the expected entropy for the probability of class membership.

Results. In agreement with simulations, psychophysical results validated that CSFs obtained with 30, 50, and 100 qCSF trials agree with conventional CSF estimates: (mean r=0.944, 0.960, and 0.976). Classification simulations showed that detecting abnormal CSFs typically took less than 10 trials and classifying specific abnormal CSFs took 20-30 trials. These adaptive Bayesian methods, generating efficient and precise CSF estimates, have clear implications for laboratory and clinical applications.

Example II

Rapid Characterization and Classification of Contrast Sensitivity Functions: the Quick CSF Methods The spatial CSF, describing grating sensitivity as a function of spatial frequency, is a psychophysical function fundamental to both basic and clinical vision science. In addition to serving as the front-end filter of spatial vision models and describing neural spatial frequency selectivity of neurons in V1, the CSF can be used to distinguish visual neuropathologies. Clinical CS testing faces several conflicting pressures. The need for short tests and application ease favors the use of cards and charts; in contrast, the need for precision and discriminative power favors psychophysical applications with better stimulus sampling—both the sampling range and grain of grating spatial frequency and grating contrast. We sought to address these needs by developing novel adaptive testing methods that (1) rapidly characterize CSFs with the precision of psychophysical testing, and (2) rapidly classify CSFs based on normal and abnormal candidate functions.

Figure 2A:
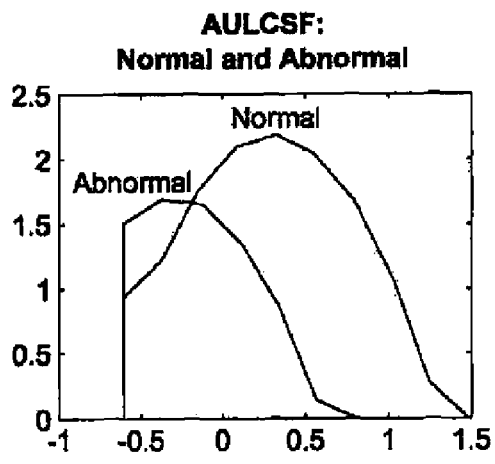
FIG. 2a presents two simulated observers and the lower panel
Figure 2B:
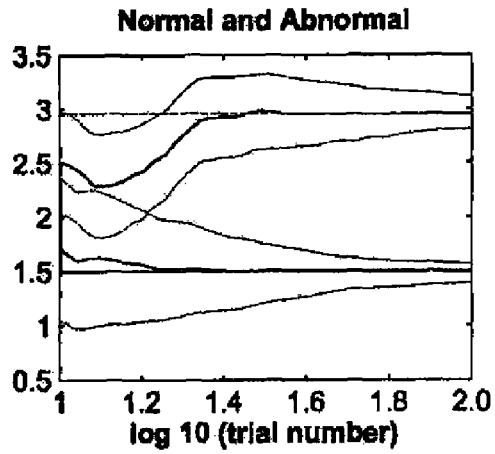
FIG. 2b shows their AULCSF estimates (mean and +/−1 s.d.) as a function of trial number.

We applied the adaptive Bayesian framework, previously used to estimate external noise functions and sensitivity (d') psychometric functions, to develop the quick CSF method. This application uses a one-step-ahead search to determine the grating stimulus (defined by spatial frequency and contrast) that minimizes the expected entropy of a posterior defined over four CSF parameters (Watson and Ahumada (2005) A standard model for foveal detection of spatial contrast. *Journal of Vision,* 5(9), 717-740; Kontsevich & Tyler, 1999, Bayesian adaptive estimation of psychometric slope and threshold. *Vision Research,* 39(16), 2729-2737; Cobo-Lewis, 1996, An adaptive method for estimating multiple parameters of a psychometric function. *Journal of Mathematical Psychology,* 40, 353-354; see FIG. 2). This parameterization (truncated log-parabola) is useful because its parameters explicitly define global CSF features: (1) peak sensitivity, (2) peak spatial frequency, (3) bandwidth at half-peak sensitivity, and (4) low spatial frequency truncation. Such feature description will make a normative dataset easier to analyze and interpret. FIG. 2a presents the normal and abnormal CSFs of two simulated observers who exhibit clear differences in area under the log CSF (AULCSF). FIG. 2b presents simulation results for testing the two simulated observers with the quick CSF method. FIG. 2b presents the AULCSF estimates for both observers as a function of trial number, with the dotted lines representing the true AULCSF values and the shaded regions representing the mean and variability (+/− one standard deviation) of AULCSF estimates. It's evident that 20-30 trials are needed to accurately measure AULCSF and distinguish normal and abnormal CSFs.

Figure 3:
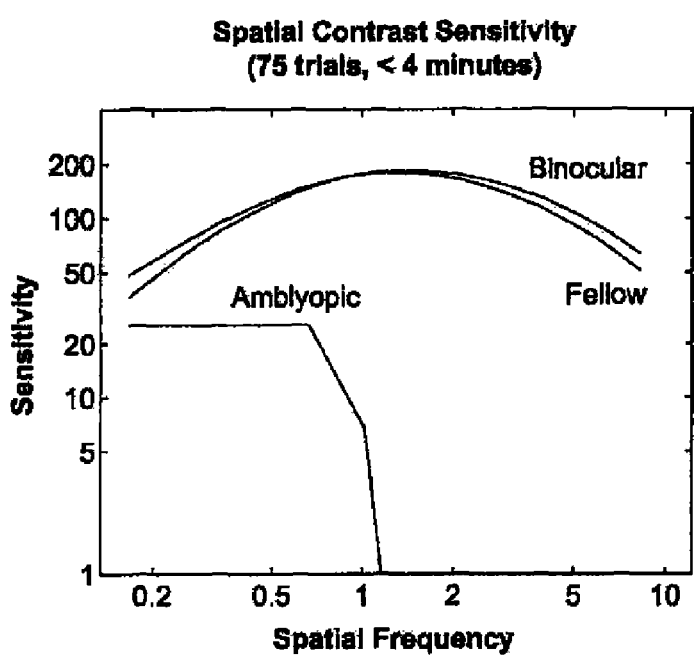
FIG. 3. An amblyopic observer tested with the quick CSF in (a) binocular, and monocular (b) amblyopic eye and (c) fellow eye conditions.

For psychophysical validation, we used an orientation discrimination task. CSF estimates obtained with the quick CSF method were validated by interleaved and independent applications of a conventional adaptive method (CAM) (Kontsevich & Tyler, 1999, Bayesian adaptive estimation of psychometric slope and threshold. *Vision Research,* 39(16), 2729-2737). We compared CSF estimates obtained with 30, 50, and 100 qCSF trials with those obtained with 30 CAM trials independently tested at each frequency (180 total trials). CSFs collected with CAM and the quick CSF exhibited excellent agreement (mean correlation coefficients >0.93 for all test lengths). To examine the quick CSF method's efficiency for characterizing abnormal vision, we measured binocular and monocular CSFs for an observer with amblyopia (see FIG. 3). The data, requiring approximately 3-4 minutes of testing per condition, demonstrates two things: (1) similar CSFs were measured in the binocular and fellow eye monocular condition, and (2) a severe CSF deficit was measured in the amblyopic eye. When measuring the CSF deficit, the qCSF method exhibited a feature that will be critical for its future clinical application. Though exhibiting a severe CSF deficit, the observer still performed at 84% correct for the test duration. By rapidly characterizing the most informative regions of stimulus space, the method avoids sampling stimulus regions that are obviously invisible and induce random guessing; the practical result is the reduction of frustration for the clinical observer.

Figure 4:
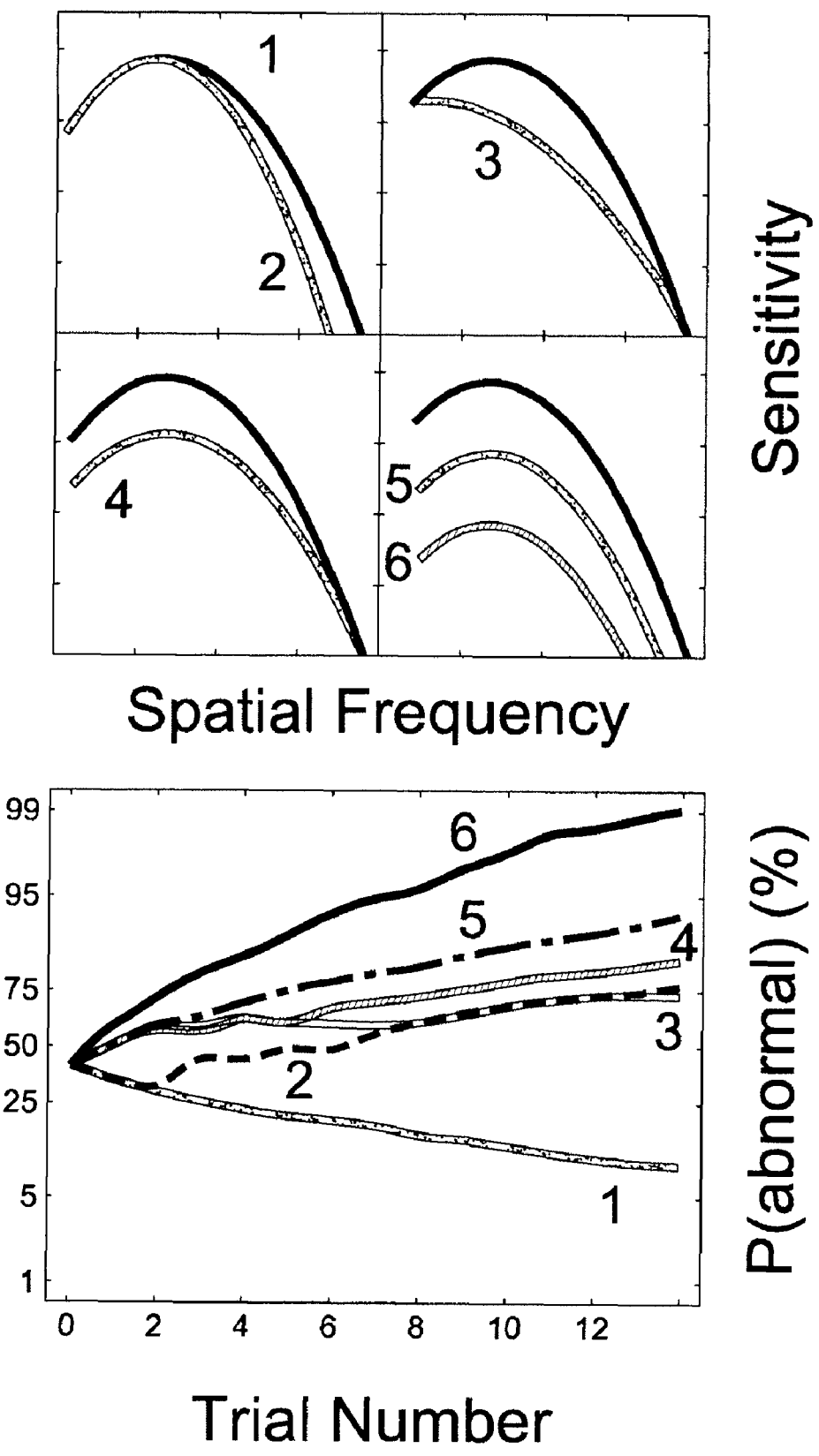
FIG. 4. In the top panel, five deficient spatial CSFs (gray) are plotted relative to a normal CSF (black). The lower panel presents results of the quick CSF's classification (screening) method. For simulated performance by each of the normal and abnormal prototypes, the probability of abnormal classification is presented as a function of trial number (prior=40%).

For clinical applications, characterizing the precise shape of an observer's CSF is less important than classifying it relative to normal and abnormal candidate functions. Regan (1991) (Spatiotemporal abnormalities of vision in patients with multiple sclerosis. In *Spatial Vision* (pp. 239-249). Boca Raton: CRC Press.) presented a rough taxonomy of normal and abnormal CSFs measured in observers with multiple sclerosis. FIG. 4 presents the normal CSF (the black dotted line), and five different patterns of CSF deficits. From left to right, top to bottom, these deficits are: (1) high spatial frequency deficit, (2) intermediate spatial frequency deficit, (3) low spatial frequency deficit, (4) small general deficit, and (5) severe general deficit. These functions demonstrate the individual differences in CSF deficits that arise in visual neuro-pathologies. To classify CSFs, we applied an adaptive classification method developed by Cobo-Lewis (1997) to classify infant audiograms. Similar to previous applications, a one-step-ahead search is used; however, instead of calculating the expected minimum expected entropy for a posterior density defined over psychometric parameters, the method calculates entropy over the posterior probability of class membership. Therefore, this method effectively maximizes the information gained about which candidate function(s) best describe the observer's CSF. This "screening" mode of the quick CSF serves as a useful complement to the characterization algorithms described above.

For a simulation of adaptive classification using the 6 CSF classes (1 normal and 5 abnormal) described above, we used priors for classification: [0.60 0.05 0.05 0.05 0.20 0.05]. These priors signify that the most likely CSF (60%) is normal (class 1), and the second mostly likely (20%) is the small general deficit (class 5) that might accompany normal aging. To generate synthetic data for simulation, we used the candidate functions (1 normal and 5 abnormal). To simplify presentation of the classification results, we only consider estimates of abnormal probability, 1-p(Normal), although the procedure actually distinguishes membership probability in the different abnormal classes. The abnormal probability results are presented in the lower panel of FIG. 4, as a function of trial number. These simulations suggest that a conservative estimate of the data needed to classify normal and abnormal CSFs is 10-20 trials (<1-2 minutes). These results suggest that the quick CSF method can be a very valuable tool for rapidly characterizing and classifying abnormal contrast sensitivity in a clinical setting.

Example III

Bayesian Adaptive Estimation of the Contrast Sensitivity Function: the Quick CSF (qCSF) Method The contrast sensitivity function (CSF), which describes grating sensitivity (1/threshold) as a function of spatial frequency, is a canonical measure of spatial vision. The CSF is clinically significant, because contrast sensitivity predicts functional vision and several visual neuro-pathologies exhibit characteristic CSF deficits. Current contrast sensitivity cards and charts simplify CSF testing by limiting the sampling range and resolution for grating stimuli. Laboratory procedures for measuring the CSF, though more precise and flexible, are too onerous for clinical use. We sought to develop a CSF procedure providing the best of both worlds: a forced-choice computerized test that estimates the entire CSF across a wide spatial frequency range with a testing time comparable to cards and charts.

The quick CSF method expands a Bayesian adaptive strategy first applied to estimate multiple parameters of the psychometric function (Cobo-Lewis, 1996; Kontsevich & Tyler, 1999). A one-step-ahead search simulates the next trial and estimates the stimulus that provides the most information about a form of the CSF defined by four parameters (Watson and Ahumada): (1) peak sensitivity, (2) peak spatial frequency, (3) full-bandwidth at half-maximum sensitivity, and (4) low spatial frequency truncation. To validate the method, observers ran the qCSF concurrently with a conventional CSF procedure that used another adaptive method (Kontsevich &

Tyler, 1999) to estimate sensitivity independently at 6 spatial frequencies. In agreement with simulations, psychophysical results validated that CSFs obtained with 25, 50, and 100 qCSF trials agreed with the conventional CSF estimates: (mean RMSE<1 dB). The qCSF can also estimate the area under the Log CSF (AULCSF) over testing times (<1-2 minutes) comparable to cards and charts. The development of an efficient procedure for rapidly measuring the CSF has clear value for laboratory and clinical applications.

Introduction

The Contrast Sensitivity Function

The contrast sensitivity function, which describes how grating sensitivity (1/threshold) varies with spatial frequency, is fundamental to vision science. Its prominence in psychophysical and physiological studies of vision is based on several factors: (1) the critical input to visual mechanisms is luminance contrast, not luminance itself (Regan, 1991b; De Valois & De Valois, 1988; Graham, 1989; Shapley & Lam, 1993); (2) contrast sensitivity in many species, from single neurons to full observers, exhibits a characteristic low- or band-pass shape (Ghim & Hodos, 2006; Uhlrich, Essock, & Lehmkuhle, 1981; Movshon & Kiorpes, 1988; Kiorpes, Kiper, O'Keefe, Cavanaugh, & Movshon, 1998), (3) linear systems analysis relates the CSF to the receptive field properties of neurons (F. W. Campbell & J. G. Robson, 1968); (4) the CSF stands as the front-end filter for standard observer models in complex visual tasks (Watson & Ahumada, 2005; Chung, Levi, & Tjan, 2005).

As a clinical measure, contrast sensitivity is important because it predicts functional vision better than other visual diagnostics (Faye, 2005). Contrast sensitivity deficits accompany neuro-pathologies, which include amblyopia (Bradley & R. D. Freeman, 1981; Hess & Howell, 1977), glaucoma (Hot, Dul, & Swanson, 2008; Ross, Bron, & Clarke, 1984), optic neuritis (Zimmern, F W Campbell, & Wilkinson, 1979), diabetic retinopathy (Della Sala, Bertoni, Somazzi, Stubbe, & Wilkins, 1985; Sokol et al., 1985), Parkinson's disease (Bodis-Wallner et al., 1987; Bulens, 1986; Mestre, 1990), and multiple sclerosis (Regan, Raymond, Ginsburg, & Murray, 1981), even when acuity or perimetry results appear normal (Woods & Wood, 1995; Arden & Jacobson, 1978). Contrast sensitivity is also an important outcome measure for refractive and cataract surgery (Ginsburg, 2006; McLeod, 2001) and visual rehabilitation programs for myopia (Tan & Fong, 2008) and amblyopia (Huang, Tao, Zhou, & Lu, 2007; Zhou et al., 2007; Levi & Li, 2009). Taken together, these studies convey the great value of CSF testing for detecting visual pathology and tracking its progression or remediation.

Measuring the Contrast Sensitivity Function

The efficiency of CSF measurement is limited by a basic tradeoff in experimental design: for sampling both grating frequency and contrast, a sufficient range is needed to capture the CSF's global shape and a sufficient resolution is needed to capture its dynamic regions (e.g., high frequency fall-off). In the laboratory, the typical CSF measurement uses an adaptive procedure (e.g., Levitt, 1971; Watson & Pelli, 1983; for reviews, see Treutwein, 1995; Leek, 2001) to dynamically change grating contrast independently across a pre-specified set of spatial frequencies. However, pre-determining the spatial frequency conditions introduces the same inefficiencies that the method of constant stimuli does for sampling signal contrasts to measure the psychometric function (Watson & Fitzhugh, 1990). Increasing the range or resolution for sampling grating frequency adds stimulus conditions, each of which requires a minimum number of experimental trials (often 50-100 trials) and increases testing time linearly. Therefore, sampling the CSF at 5-10 spatial frequencies typically requires 500-1000 trials (30-60 minutes). This amount of data collection, reasonable for experiments measuring a single CSF, becomes prohibitive for measurement of multiple CSFs (e.g., in different eyes or at multiple temporal frequencies).

The difficulties of measuring the full CSF are exacerbated in the clinical setting. Due to severe testing time constraints, clinical contrast sensitivity tests are far more condensed, and less precise, than laboratory procedures. The most-preferred contrast sensitivity test, the Pelli-Robson chart (Pelli, Robson, & Wilkins, 1988), does not use gratings; instead, it varies the contrast of constant-size letters. Although this test detects the general deficits in contrast sensitivity exhibited by cataract, macular degeneration, and diabetic retinopathy (Ismail & Whitaker, 1998), this test does not provide detailed frequency specific information, due to the broadband frequency spectra of its letter stimuli (Ginsburg, 2003). To isolate spatial frequency channels and identify frequency-specific deficits, alternative CS tests (Arden, FACT, and Vistech) vary both the frequency and contrast of narrowband gratings (Arden & Jacobson, 1978; Ginsburg, 1984). For portability and ease of application, these tests use paper media that restricts testing to a small number (1-4) of frequencies and a small number (5-9) of contrast levels. This naturally limits the dynamic range and precision for measuring contrast sensitivity phenomena.

There are several factors suggesting that current contrast sensitivity tests will require more flexibility and precision to meet emerging clinical needs (Elliott, Sanderson, & Conkey, 2007): (1) Although some disorders (e.g., anisometropic amblyopia) exhibit a stereotypic frequency-specific deficit, others can exhibit a spectrum of low, high, or intermediate deficits across subjects (Regan, 1991). The variability in CSF deficits, exhibited between and within visual pathologies, suggests that measuring the full CSF over a wide frequency range is clinically important. (2) Contrast sensitivity deficits exhibited at specific temporal frequencies (Tyler, 1981; Tyler, Hardage, & Stamper, 1994) suggests the importance of measuring more than just the static CSF measured by cards and charts. (3) For functional validity, it's important that contrast sensitivity be tested under the diverse conditions encountered in activities of daily life: day and night illumination, with and without glare. (4) For prospective vision therapeutics, that will eventually treat focal retinal damage with stem cells (Bull, Johnson, & Martin, 2008; Kelley et al., 2008) or neural prosthetics (Colby, Chang, Stulting, & Lane, 2007; Dowling, 2008; Weiland, Liu, & Humayun, 2005), it will be critical to measure the progression or remediation of contrast sensitivity at isolated retinal loci. This will require a test with the flexibility to target contrast sensitivity measurement to retinal loci, rather than a chart that exclusively tests foveal sensitivity.

Clinical CSF tests need to be rapid, with enough flexibility to capture normal and abnormal vision across different testing conditions, and to follow the progression or remediation of visual pathology. Current cards and charts are not flexible enough to adequately capture the range of normal and abnormal CSFs observed across different illumination and glare conditions, temporal frequencies, and retinal loci. To meet these needs and develop an "ideal" contrast sensitivity test, a first important step is using a computerized display, which provides the stimulus flexibility and precision to distinguish between normal and abnormal vision, and even different types of abnormal vision. To meet the strong constraint of short testing times (challenged by adding more possible stimuli), a computerized test provides the advantage of adaptive testing strategy that needs no experimenter input. In addition to the adjustment of signal contrast typical for adaptive methods, the ideal testing strategy would choose the stimulus for the next trial by evaluating both the frequency and contrast of possible grating stimuli. A forced-choice task would be useful for avoiding the response criterion issues inherent in detection tasks. This issue is especially important for testing the progress of visual rehabilitation: it's critical to determine that patients are improving their contrast sensitivity, and not only "learning" different response criteria.

The Current Study

To improve the measurement of contrast sensitivity, the current study develops the quick CSF (qCSF) method, a monitor-based, computerized test that provides the precision and flexibility of laboratory psychophysics, with a testing time comparable to clinical cards and charts. Relative to previous contrast sensitivity tests, the qCSF uses a much larger stimulus space that exhibits both a broad range and fine resolution for sampling grating frequency and contrast. Whereas classical adaptive methods (e.g., QUEST or weighted up-down staircases) converge to estimate a single threshold, the qCSF estimates the entire CSF at once, using Bayesian inference and a trial-to-trial information gain strategy. Before each trial, a one-step-ahead evaluates the next trial's possible outcomes, and finds the stimulus providing the most information about the parameters of the CSF. This test strategy finds informative stimuli by leveraging information acquired during the experiment with a priori knowledge about the general form of the CSF. In this report, demonstration and simulation of the qCSF method is followed by validation results obtained in a psychophysical experiment.

The Quick CSF Method

Characterizing the Contrast Sensitivity Function

Figure 5:
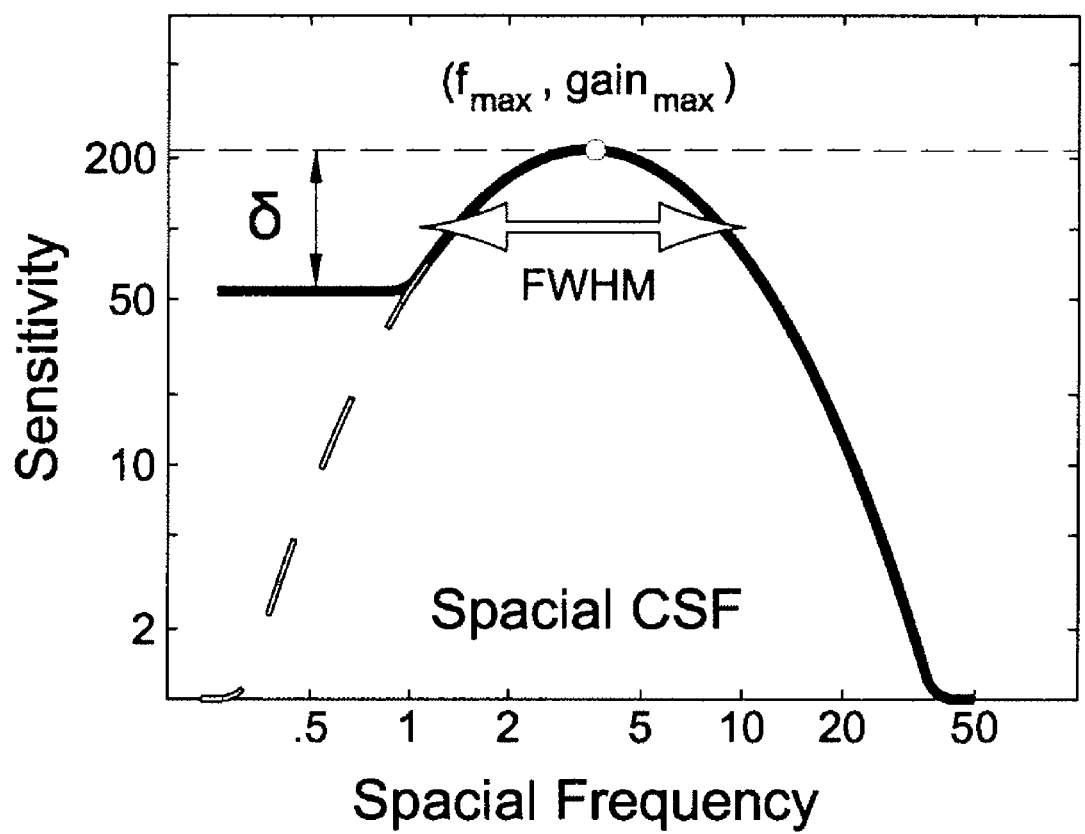
FIG. 5. The spatial contrast sensitivity function is described by four parameters: (1) the peak gain, (2) the peak frequency, (3) the bandwidth, full-width at half-maximum, and (4) the truncation level on the low-frequency side.

The contrast sensitivity function, S(f), represents sensitivity (1/threshold) as a function of grating frequency. To describe the CSF's global shape, the truncated log-parabola (Watson & Ahumada, 2005; see FIG. 5) uses four parameters: (1) the peak gain (sensitivity) $\gamma_{max}$; (2) the peak spatial frequency, $f_{max}$; (3) the bandwidth, $\beta$, which describes the function's full-width at half-maximum (in octaves), and (4) $\delta$, the truncation level at low spatial frequencies. Without truncation, the log-parabola, S'(f), defines (log) sensitivity as:

$$S'(f) = \log_{10}(\gamma_{max}) - \kappa\left(\frac{\log_{10}(f) - \log_{10}(f_{max})}{\beta'/2}\right)^2 \quad (1)$$

where $\kappa=\log_{10}(2)$ and $\beta'=\log_{10}(2\beta)$. FIG. 5 represents the log parabola without truncation with a dotted line. The parabola is truncated at low frequencies with the parameter $\delta$:

$$S(f)=S'(f) f>f_{max}$$

$$S(f)=\log_{10}(\gamma_{max})-\delta f<f_{max} \text{ and } S'(f)<\gamma_{max}-\delta \quad (2)$$

This function exhibits several advantages over other parametric forms of the spatial CSF. Rohaly & Owsley (1993) noted that two functional forms of the CSF defined by three parameters—double-exponential and (untruncated) log-parabola—were adequate for fitting CSF data pooled across subjects, but systemically misfit individual data. The asymmetric exponential function misfits the symmetry typically observed near the CSF's peak, and the symmetric log-parabola misfits the truncation (flattening) typically observed on the low-frequency side (<0.5 cpd). With its additional parameter, the truncated log-parabola can deal with issues of asymmetry. Other CSF forms described by four parameters, such as the difference of Gaussians, provide equivalent fits to CSF data (Watson & Ahumada, 2005), but their fitted parameters are not immediately interpretable. The interpretable parameter set provided by the truncated log-parabola will be especially useful for a potential normative CSF dataset, which in turn can provide Bayesian priors for qCSF testing.

Bayesian Adaptive Parameter Estimation

The classical Bayesian adaptive method, QUEST, was designed to measure a single threshold on the psychometric function (Watson & Pelli, 1983). Methods later developed for adaptively estimating the threshold and steepness of the psychometric function (Cobo-Lewis, 1997; Kontsevich & Tyler, 1999) have since been extended to measure more complex psychophysical functions with relatively simple functional forms (Kujala & Lukka, 2006; Lesmes, Jeon, Lu, & Dosher, 2006; Vul & MacLeod, 2007). We have used this framework to develop adaptive methods for estimating threshold versus external noise contrast functions (Lesmes et al, 2006) and sensitivity thresholds and response bias(es) in Yes/No and Forced-Choice detection tasks (Lesmes et al, submitted). In the current study we apply Bayesian adaptive inference to estimate the parameters of the contrast sensitivity function. The qCSF's stimulus placement strategy uses a one-step-ahead search to determine the grating stimulus (defined by spatial frequency and contrast) that minimizes the expected entropy of a posterior defined over the CSF parameters (see FIG. 5). To validate this method, the current report presents simulations and a psychophysical experiment.

Demonstration and Simulation

In the qCSF, a Bayesian prior is defined over a four-dimensional gridded space of CSF parameters. Following each trial, the prior is updated via Bayes' rule, based on the subject's response to the presented grating stimulus. Before each trial, the grating stimulus is determined by a one-step-ahead search, over the space of possible stimuli jointly defined by grating frequency and grating contrast, estimates the expected information gain for each possible stimulus. The presented stimulus is one that provides maximum information gain. The detailed pre- and post-trial calculations are described in the Appendix and MATLAB implementation is provided as supplementary material.

FIG. 5 presents a prototypical CSF (Watson & Ahumada, 2005), with peak gain $\gamma_{max}$=200, peak frequency=2.5 cpd, bandwidth=3 octaves, and low-frequency truncation at 0.6 decimal log units below the peak.

The parameter space for the qCSF is a grid. For the different parameters, the possible ranges were: 1.2 to 1200 for peak gain, 0.25 to 24 for peak frequency, 0.25 to 8 octaves for bandwidth, and 0.01 to 4 log units for truncation level. The marginal priors, defined over each of these ranges, were symmetric on the log parameters and relatively flat (see Appendix). The prior modes for the respective parameters were 100, 2.5 cpd, 3 octaves, and 1.5 log units for truncation. The joint prior was the normalized product of marginal priors, independent (separable) across different parameters.

Figure 6:
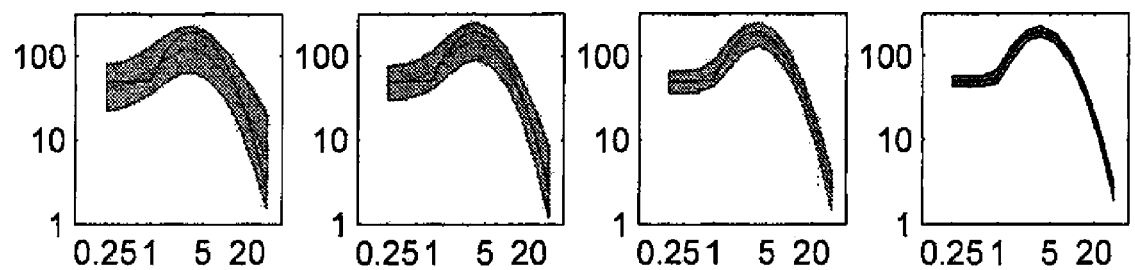
FIG. 6. CSF estimates obtained with 25, 50, 100, and 300 trials of the qCSF method. The general shape of the CSF is evident with as few as 25 trials, but imprecision is reflected in shaded regions, which reflect +/−1 standard deviation for individual sensitivity estimates. With increasing trial numbers (50-300 trials), method convergence is supported by (1) the increasing concordance of average qCSF estimates (red line) and the true CSF (blue line), and (2) the decreasing area of the error regions.

FIG. 6 summarizes the results of 1000 qCSF iterations. Even as few as 25-50 trials (distributed over 12 possible spatial frequencies) provide a general assessment of the CSF's shape, although estimates obtained with such few trials are not very precise: mean variability ≈4-6 dB. With 100 trials of data collection, CSF estimates are unbiased and reach 2-3 dB precision.

Figure 7:
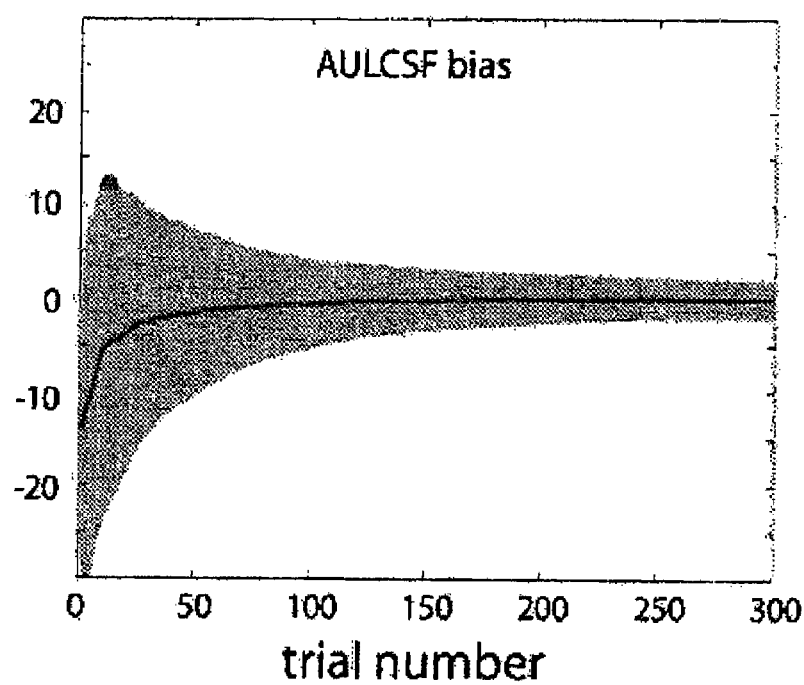
FIG. 7. The convergence of AULCSF estimates obtained with the qCSF. ALUCSF bias is presented in % units: (true AULCSF−estimated AULCSF)/true AULCSF. On average, these CSFs can be distinguished with as few as 25 trials, but CSF estimation is imprecise. The method's convergence is evident in the decreasing area of error regions (+/−1 standard deviation) as more trials are collected.

The precise measurement of individual contrast thresholds provided by 100-300 qCSF trials is impossible (and unnecessary) for clinical measures of vision. More typical is the use of specific CSF features (e.g., peak sensitivity, peak spatial frequency, or grating acuity) as surrogates for the full contrast sensitivity function. However, by focusing on local CSF features, these metrics ignore large CSF regions; therefore, a better comprehensive metric is provided by the area under the log CSF (AULCSF), which Fergus Campbell described as "our visual world" (Campbell, 1983). FIG. 7 presents the bias of AULCSF estimates obtained with the qCSF as a function of trial number. These results demonstrate that the bias of AULCSF estimates decreases below 10% after 25 trials, and that AULCSF variability (evaluated via the coefficient of variation) decreases from 15% to 10%, between 25 and 50 trials of data collection. With more trials, bias mean and variability both decrease. Thus, even though estimates of the full CSF with 25 qCSF trials are imprecise, reasonably accurate and precise AULCSF estimates can be obtained with such few trials: bias <10% after and coefficient of variation <15%.

Figure 8:
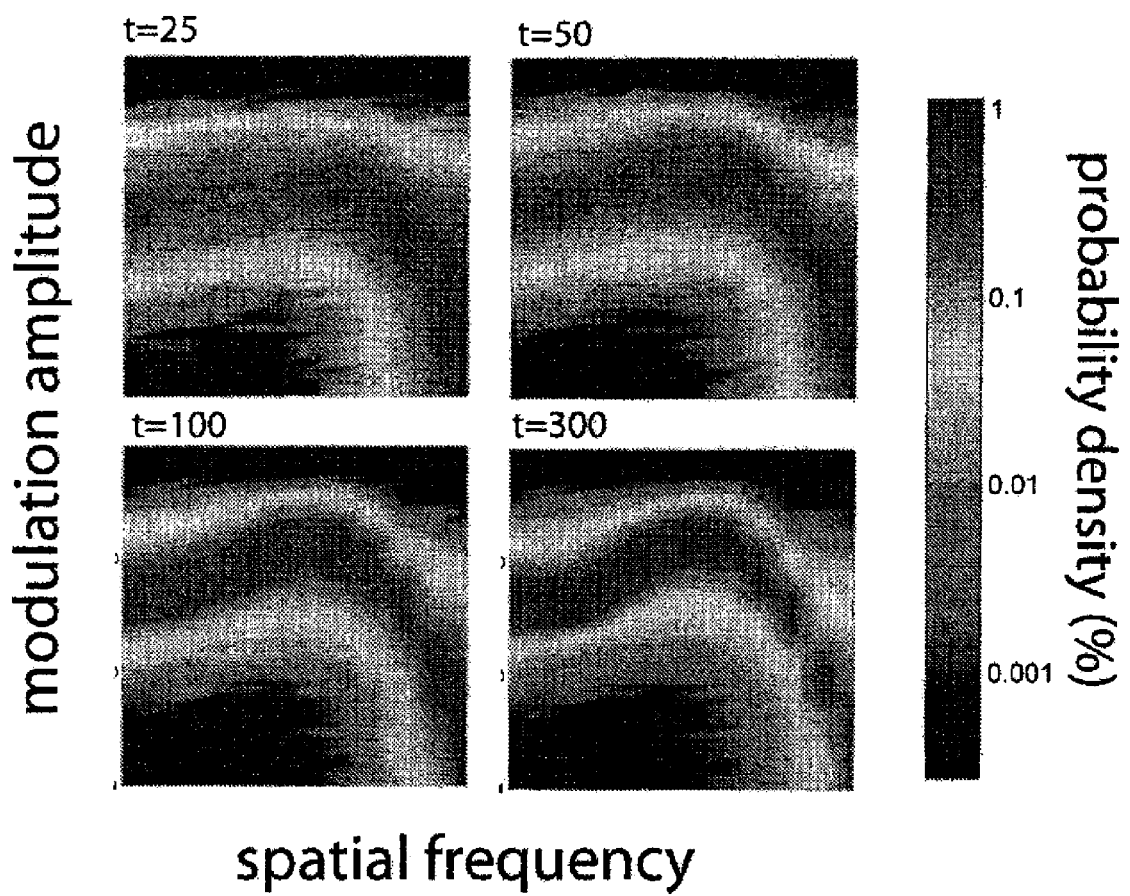
FIG. 8. Probability density histograms for four epochs of a qCSF session. Over the course of a session, stimulus presentation focuses on the true CSF.

The qCSFs pattern of stimulus presentation is summarized by the two-dimensional stimulus histograms presented in FIG. 8. Each histogram presents the probability (density) of stimulus presentation, as a function of grating frequency and contrast, for four data collection endpoints: 25, 50, 100, and 300 trials.

Simulation results support the qCSF as a promising method for rapidly estimating the contrast sensitivity function. Given a data collection rate of 15-20 trials/minute, reasonably precise CSF estimates can be obtained in 5-10 minutes. This testing time is far less than the 30-60 minutes required of previous CSF measurements. Moreover, simulations suggest that only 1-2 minutes are needed to estimate the comprehensive CSF metric provided by the AULCSF. Relative to previous AULCSF measures, which used coarse sampling of grating frequency (provided by the FACT test), those obtained with the qCSF will be more flexible and precise.

Psychophysical Validation

For psychophysical validation of the qCSF, we used an orientation identification task. We evaluated precision through test-retest comparisons and accuracy through independent CSF measurements obtained with the $\psi$ method developed by Kontsevich & Tyler (1999).

Method
Apparatus

The experiment was conducted on a Windows-compatible computer running PsychToolbox extensions (Brainard, 1997; Pelli, 1997). The stimuli were displayed on a Dell 17-inch color CRT monitor updating at a 120 Hz refresh rate. A special circuit changed the display to a monochromatic mode, with high grayscale resolution (>12.5 bits); luminance levels were linearized via a lookup table (Li et al, 2002). Stimuli were viewed binocularly with natural pupil at a viewing distance of approximately 150 cm in dim light.

Participants

Two naïve observers and one of the authors of this report participated in the experiment. All observers had corrected-to-normal vision and were experienced in psychophysical studies.

Stimuli

The signal stimuli were Gaussian-windowed sinusoidal gratings, oriented $\theta=\pm 45$ degrees from vertical. The luminance profile of the Gabor stimulus is described by:

$$L(x,y)=L_0\{1.0+c \times \sin[2\pi f(x \cos \theta + y \sin \theta)] \times e^{-(x^2+y^2)/2\sigma^2}\} \quad (20)$$

where c is the signal contrast, $\sigma=0.6$ deg. The signal stimuli were rendered on a 64×64 pixel grid, extending 2.08×2.08 deg of visual angle. For qCSF trials, the 11 possible grating spatial frequencies were spaced log-linearly from 0.6 to 20 cpd; the 46 possible grating contrasts spaced log-linearly from 0.15% to 99%. The stimulus sequence started with presentation of a fixation-cross in the center of the screen for 500 ms, followed by a verbal cue, "small," "medium" or "large," to the stripe size of the imminent grating stimulus. The cue was used to decrease stimulus uncertainty, which especially affects sensitivity measures in the high-cutoff region (Woods, 1996). The stimulus was presented for 250 ms.

Design and Procedure

Observers ran four testing sessions, each lasting approximately 30-40 minutes. During each session, two qCSF runs, which each lasted 100 trials, were applied in succession. Interleaved with qCSF runs were trials implementing another adaptive procedure (Kontsevich & Tyler, 1999), applied independently in 6 spatial frequency conditions. There were 30 trials in each spatial frequency condition. To summarize, for each observer, each of four total sessions consisted of 2×100=200 qCSF trials and 6×30=180 $\psi$ trials. Over the course of the experiment, this corresponded to collecting eight total qCSF measures and four $\psi$-CSF measures for each observer. The priors used for CSF parameters are presented in the Appendix.

Results
Accuracy

Figure 9:
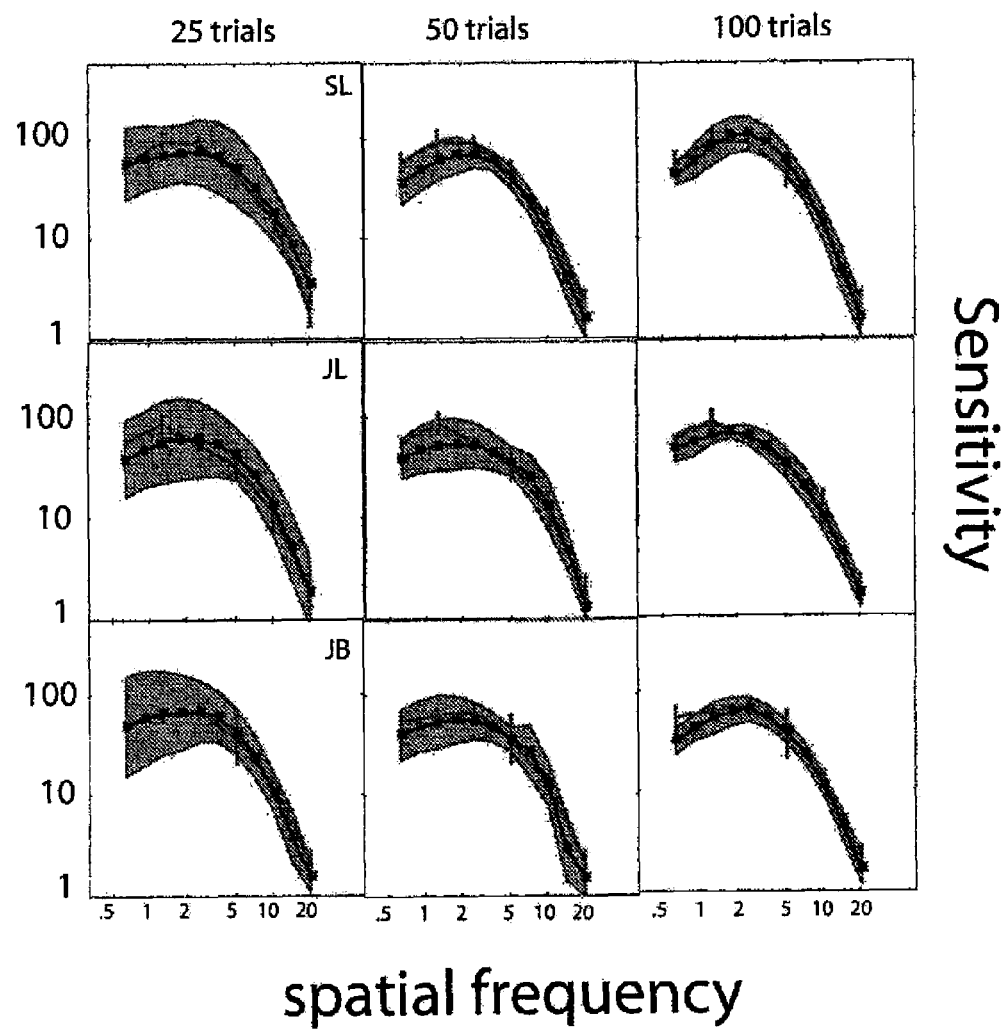
FIG. 9. Spatial CSFs obtained with 2 independent procedures: the qCSF and the ψ method. Sampling resolution of spatial frequency is twice as high using the qCSF. Functions were collected with the qCSF method (blue markers and lines) and ψ method (red lines). qCSF runs were collected with either 25, 50, or 100 trials. The gray-shaded region reflects the variability of qCSF estimates, and the red error bars reflect variability of ψ method estimates.

FIG. 9 presents the CSFs measured with the qCSF (blue lines) and $\psi$ method (red lines). Each row presents CSF data from a different observer, and each column presents qCSF estimates obtained with different numbers of trials: 25, 50, and 100. The error region (shaded gray) represents the qCSF variability (mean±1 s.d) for estimating individual thresholds. For comparison, for each observer, the same $\psi$-CSF estimate, obtained with the maximum trial number, is presented across all columns; error bars represent variability (±1 s.d). Initial examination of CSFs obtained with both methods suggests significant overlap. To quantify the concordance of CSF estimates, we calculated the root mean squared error (RMSE) of the mean thresholds obtained with the two methods, collapsed across all three observers (m=3) and spatial frequency conditions (n=6) common to both methods:

$$RMS_{error} = \sqrt{\frac{\sum_m \sum_n (qCSF(m,n) - \psi(m,n))^2}{(m \times n) - 1}}$$

The mean error between sensitivities estimated with both methods, as a function of qCSF trial number (25, 50, and 100 trials) was 0.109, 0.125, and 0.099.

Precision

Evidence for the qCSF's convergence is provided by the decreasing variability of threshold estimates as a function of trial number. For sensitivity estimates obtained with 100 qCSF trials, the average threshold variability across the 11 frequency conditions was 2.79 dB (sd=0.63). The threshold variability exhibited by the $\psi$ method was 2.25 dB (s.d.=1.04). CSF estimates obtained with the $\psi$ method were more precise, but also required more data collection for each CSF: 180 vs 100 trials. For a fair comparison, when CSF estimates obtained with the $\psi$ method were calculated using 102 trials per CSF (16 per each of 6 spatial frequency conditions), threshold variability was 4.5 dB.

Figure 10A:
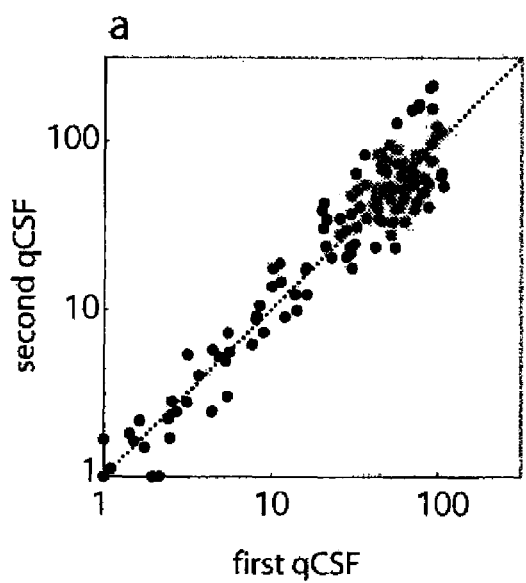
FIG. 10. Test-retest comparisons for two qCSF runs applied in the same testing session. (a) Contrast sensitivities measured with the second qCSF run plotted against those obtained in the first run, with 100 trials. The Pearson correlation coefficient for these comparisons averaged r=96% (sd=4%). (b) Bland-Altman Analysis presents the differences between sensitivity estimates, plotted against their mean. Mean difference <0.01 log units and the standard error of the difference was 0.3 log units. Assuming that both measures contribute equally to the variance of the difference suggests a variability estimate per measurement of 0.12 log units=2.4 dB.
Figure 10B:
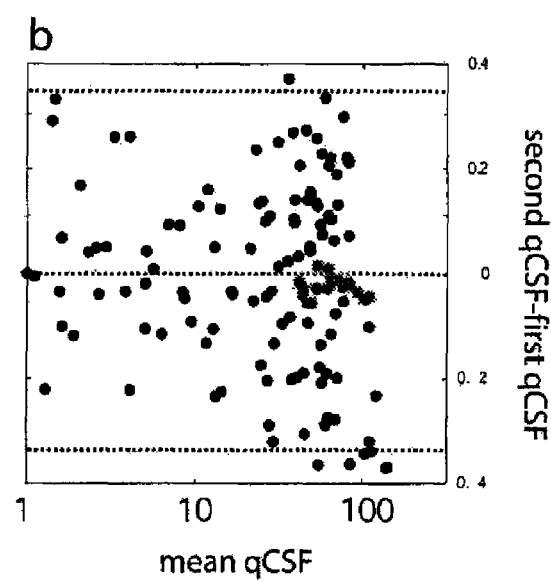

Two qCSF runs were applied in each session. FIG. 10a plots sensitivities estimated from the second qCSF run against those from the first. The average test-retest correlations for the two CSFs estimated in each session, with 25, 50, and 100 qCSF trials were 81.7% (sd=21%), 88% (sd=11%), and 96% (sd=4%). Though test-retest correlations are widely reported, they are not the most useful way to characterize method reliability or agreement. FIG. 10b presents Bland-Altman Analysis that plots the difference of two qCSF estimates against their mean. The mean and standard deviation of test-retest differences were 0.0075 and 0.1745 (3.49 dB). These results signify that (1) sensitivity measures do not change systematically over the course of single testing sessions and (2) the precision of test-retest differences within sessions agrees with estimated across single tests: compare 3.49 dB with $\sqrt{2.79^2+2.79^2}=3.94$ dB.

Figure 11:
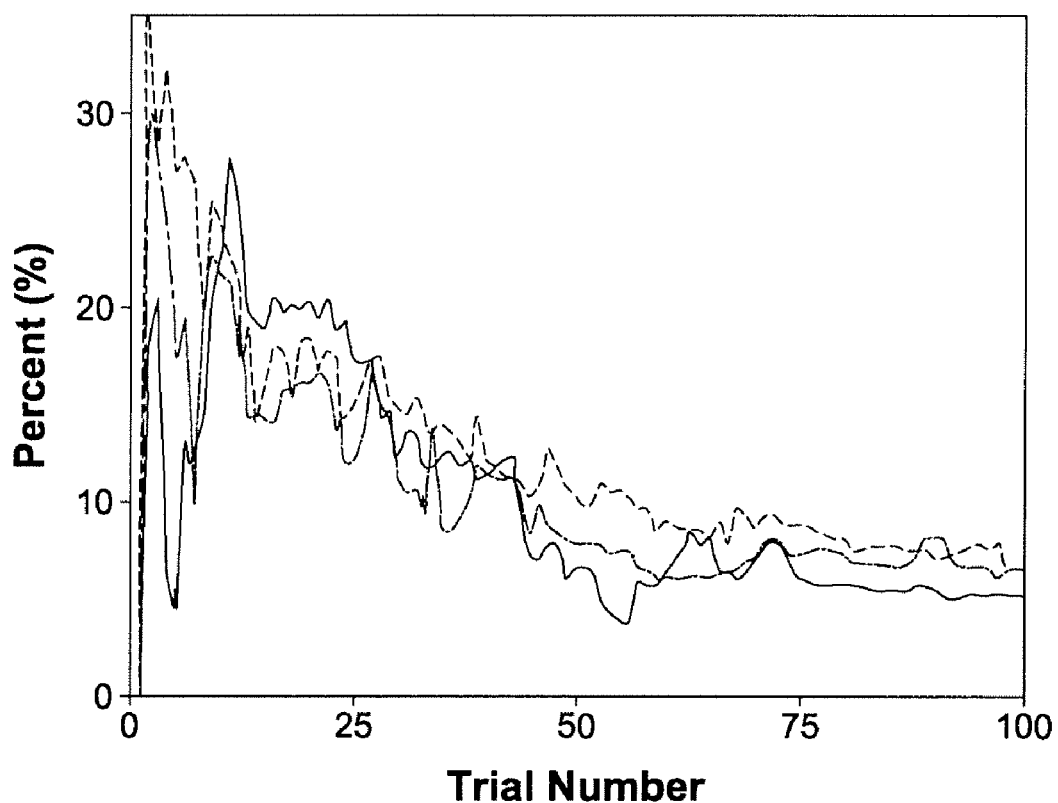
FIG. 11. Variability of AULCSF estimates obtained in a qCSF psychophysical validation from three observers. Convergence in AULCSF estimates is indicated by the consistently decreasing variability as a function of trial number.

To demonstrate the convergence of AULCSF estimates obtained with the qCSF, FIG. 11 presents the coefficient of variation of AULCSF estimates as a function of trial number, for each subject. The consistent pattern, exhibited by each subject, is a decrease in variability as the trial number increases: from approx 15% after 25 trials, to 5% after 100 trials. These measures exhibit excellent agreement with those predicted by simulations.

Discussion

For psychophysical validation, we compared CSF estimates obtained with 25, 50, and 100 qCSF trials with those obtained with an independent adaptive method (Kontsevich & Tyler, 1999). CSFs collected with the qCSF and the ψ method exhibited excellent agreement. As suggested by simulations, only 25 trials (<2 min) were sufficient to estimate a gross comprehensive CSF metric, but more precise estimation of sensitivities at each tested frequency required more time (5-15 minutes).

General Conclusion and Discussion

The qCSF applies a Bayesian adaptive strategy that uses a priori knowledge about the CSF's general form to maximize the information gained about the observer during a psychophysical test. We believe the qCSF method can meet the different needs for measuring contrast sensitivity in basic and clinical vision applications. Laboratory applications of the qCSF will be potentially valuable for comprehensive models of spatio-temporal vision (Carney et al., 1999; Tyler et al., 2002), that must account for contrast sensitivity as a function of temporal frequency (Kelly, 1979; Vannes, Koenderink, Nas, & Bouman, 1967), eccentricity (Watson, 1987; Wright & Johnston, 1983; Koenderink, Bouman, Buenodemesquita, & Slappendel, 1978), external noise (Nordmann, R. D. Freeman, & Casanova, 1992; Huang et al., 2007), or visual pathology (Regan, 1991b; Stamper, 1984).

For the most basic clinical measure of contrast sensitivity, the Pelli-Robson chart may be sufficient. However, Ginsburg (1996) critically noted that the chart's broadband letter stimuli cannot isolate spatial-frequency channels and identify frequency-specific deficits. For example, observers with recognized frequency-specific deficits to gratings (as in amblyopia or X-linked retinoschisis) exhibit normal results when tested with letters for Snellen acuity (Huang et al., 2007) or Pelli-Robson contrast sensitivity (Alexander, Barnes, & Fishman, 2005). The need for a rapid and efficient grating test is further reinforced by the FDA's guidelines for novel therapeutic devices for vision (Ginsburg, 2006). As a critical outcome measure for clinical trials, contrast sensitivity must be measured with and without glare at four spatial frequencies: 3, 6, 12, and 18 cpd for photopic (85 $cd/m^2$) and 1.5, 3, 6, and 12 cpd for mesopic (3 $cd/m^2$) vision. However, a recent study (Pesudovs, Hazel, Doran, & Elliott, 2004) of contrast sensitivity outcomes of refractive and cataract surgery illustrates the shortcomings of two current grating charts (FACT, Vistech). The limited contrast range of these charts makes them vulnerable to ceiling and floor effects: applied following refractive surgery, 33% and 50% of subjects demonstrated maximum sensitivity at the two lowest spatial frequencies; conversely, up to 60% of patients screened for cataracts with the same chart exhibited minimal sensitivity. Other recent studies comparing multiple contrast sensitivity tests (van Gaalen, Jansonius, Koopmans, Terwee, & Kooijman, 2008; Buhren, Terzi, Bach, Wesemann, & Kohnen, 2006) likewise conclude that none adequately meet the emerging needs of contrast sensitivity testing. To compare with the 45 grating stimuli used by the FACT, the qCSF can sample (at a minimum) a set of 60 contrasts×12 spatial frequencies=720 grating stimuli, with grating contrast sampled over a range of 3 log units (60 dB) with 1 dB resolution and grating frequency sampled over a range of 0.5-1 log units with 3 dB resolution. We believe that qCSF is both flexible enough to capture large-scale changes of contrast sensitivity and precise enough to capture small-scale changes common to the progression or remediation of visual pathology. With its broad range and fine resolution for stimulus sampling, the qCSF needs no experimenter input to measure CSF phenomena across widely varying testing conditions.

It will be important to measure the surface of spatio-temporal contrast sensitivity, which describes how the shape of the contrast sensitivity function varies with spatial and temporal frequency (Kelly, 1979). Such work will benefit from a novel procedure we have developed (Lesmes, Gepshtein, Lu, & Albright 2009) for rapidly estimating the spatio-temporal contrast sensitivity surface. At each "node" in the spatio-temporal frequency space, sensitivity can be characterized by several different cross-sections: (a) spatial CSFs measured at constant temporal frequency, (b) temporal CSFs measured at a constant spatial frequency, or (c) constant-speed CSFs that co-vary spatial and temporal frequency. The quick Surface (or qSurface) method elaborates the qCSF's current testing strategy in a notable way. The difficulty of measuring contrast sensitivity across multiple spatio-temporal conditions means that typical investigations of the contrast sensitivity surface focus on only one cross-section. Unlike the qCSF, which evaluates possible stimuli for their contribution to a single CSF estimate, the qSurface method evaluates grating stimuli (defined by contrast and spatial and temporal frequency) for the total information they provide about multiple possible cross-sections through the spatio-temporal sensitivity surface. This innovation, which greatly reduces the testing time for estimating spatio-temporal sensitivity, should be a valuable tool for finding the most valuable spatio-temporal condition(s) for CSF clinical testing.

The current application uses a testing strategy that minimizes expected entropy, but alternatives that minimize expected variance (Snoeren & Puts, 1997; Vul & MacLeod, 2007) or maximize Fisher information (Remus & Collins, 2007) are also likely to be successful.

It is useful to perturb the stimulus search, so it can avoid local minima, and both explore and exploit diverse regions of the stimulus space. One can conceptualize the most informative experiment as the one that maximizes the information gained over the course of the whole experiment. These methods approximate this approach by finding the most informative stimulus on each trial, but the two experimental trajectories/objectives are not the same. It will be interesting to track the development of statistical tools that search ahead more than one trial, and maybe even over the whole experiment. In light of the ongoing development in the area of optimal sequential design, we note that, in the case of the contrast sensitivity function, the qCSF procedure provides a lower bound on the most informative experiment.

Figure 12:
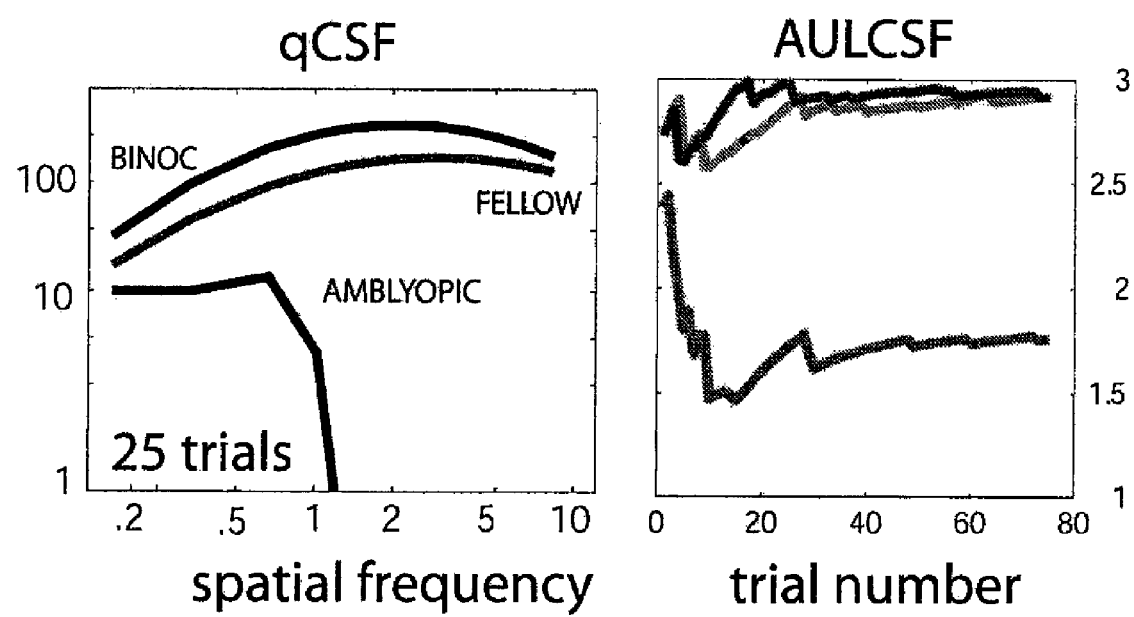
FIG. 12. Applying the qCSF to measure contrast sensitivity in amblyopia. In an amblyope, spatial CSFs were measured in three conditions: (1) one binocular CSF; (2) one monocular CSF measured in the amblyopic eye; and (3) one monocular CSF measured in the fellow eye. (a) Spatial CSFs obtained with only 25 trials are presented. (b) The severe contrast sensitivity deficit is apparent in the AULCSF estimate with as few as 10 trials. AULCSF estimates are approximately stable after 25 trials. One important feature of the qCSF's stimulus placement strategy is its high evoked performance rate: this observer completed a total of 75 trials at a comfortable performance level of 84%.

In the current study, we applied a testing strategy that rapidly characterizes the global shape of spatial contrast sensitivity functions by combining Bayesian inference and a trial-to-trial information-gain strategy. The qCSF offers the "best of both worlds" for laboratory and clinical measures of contrast sensitivity. Over psychophysical testing times of 10-20 minutes, short by historical standards, the qCSF can precisely measure the entire CSF over the wide range of spatial frequencies. For testing times comparable to that of cards and charts (<5 min), the qCSF is useful for estimating the area under the log CSF (AULCSF) with good precision (c.v.=15%). FIG. 12a presents the results of a preliminary application to characterize the CSF deficit of an amblyopic observer using the qCSF. The method distinguishes normal and abnormal CSFs with as few as 25 trials, with a stimulus placement strategy that minimizes the observer's frustration level. Our more systematic validation of the qCSF method on adults with amblyopia has also been a success (Hou, Huang, Lesmes, Lu, & Zhou, in preparation).

The qCSF is part of the emergence of a new generation of adaptive methods, which exploit advances in personal computing power to increase the complexity of classical Bayesian adaptive testing strategies (Benda, 2007). These methods estimate increasingly elaborate psychophysical models, which include the estimation of multiple parameters of the psychometric function (Tanner, 2008), equi-detectable elliptical contours in color space (Kujala & Lukka, 2006); the features of external noise functions (Lesmes, Jeon, Lu, & Dosher, 2006), the spatio-temporal contrast sensitivity surface (Lesmes, Lu, Baek, & Albright, 2008), the discrimination of different models of memory retention (Myung & Pitt, in press), and models of neural input-output relationships (Lewi, Butera, and Paninski, 2007; Paninski, 2005). Taken together, these methods provide a powerful and versatile approach that is especially useful for studying phenomena previously restricted to data-intensive applications. Their computationally principled approach to intuitive data collection strategies will make them valuable in many future applications.

APPENDIX A

Initializing the Quick CSF

For the qCSF, it's necessary to first define a discrete, gridded parameter space, $T_\theta$, that consists of four-dimensional vectors $\theta=(f_{max},\gamma_{max},\beta,\delta)$, which represent the full range of CSFs that potentially characterize the test observer. Before the experiment starts, a prior probability density, $p(\theta)$, which reflects baseline knowledge about the observer's CSF, is defined over the space, $T_\theta$. The prior can be informed by knowledge about the task or the test population. For example, although the gain and frequency of the CSF's peak can vary greatly across subjects, there is less variability in its bandwidth.

FIG. 13 presents the priors (defined by hyperbolic secant functions; King-Smith et al., 1997) for each of the four CSF parameters, used in the current psychophysical validation. For comparison, the posterior obtained one concluded session is also presented. The marginal prior, $p(\theta_i)$, for each parameter i=1, 2, 3, 4, was defined by the best guess for that parameter (mode) and the confidence (width) of that guess:

$$p(\theta)=sech(\theta_{confidence} \times (\theta-\theta_{guess}))$$

The joint prior was defined as the normalized product of the marginal priors.

Stimulus Selection

To choose the grating stimulus, s, presented on each trial t, the qCSF method applies a strategy that minimizes the expected entropy of the Bayesian posterior defined over psychometric parameters (e.g., Kontsevich & Tyler's ψ method). The experimental data reported in this paper were collected with the pre-trial calculations prescribed by Kontsevich & Tyler, but the provided implementation combines elements of the ψ method and an equivalent re-formulation (Kujala & Lukka, 2006). Kujala and Lukka reformulated the calculation of minimum expected entropy, by focusing on the equivalent task of maximizing the expected information gain between prior and posterior. Using a cost function based on the expectation of entropy change provides a great advantage: Monte Carlo sampling of the prior can be used to approximate expected information gain, by calculating the expected information gain over Monte Carlo samples. This approximation affects the precision of parameter estimates only minimally. For sampling the prior, Kujala and Lukka used Monte Carlo Markov chain sampling, which greatly reduces computing load by forgoing explicit maintenance of the prior. In our application, we sample the discrete prior over a gridded parameter space.

Before each trial, the grid-defined prior is sampled via Monte Carlo inverse sampling, using the MATLAB function "discretesample.m", written by Dahua Lin, and available for download from the MATLAB Central file exchange (see the website: www.mathworks.com/matlabcentral/fileexchange/21912). The number of samples can be arbitrarily high (depending on your computer), though simulations suggest that as few as 50-100 samples are sufficient for method convergence. As prescribed by Kujala and Lukka (2006), for each possible stimulus x the calculation of information gain is:

$$I_t(\Theta; R_s) = H_t(R_s) - H_t(R_s | \Theta)$$
$$= h\left(\int p_t(\theta)\Psi_\theta(x)d\theta\right) - \int p_t(\theta)\Psi_\theta(x)d\theta$$
$$\approx h\left(\frac{1}{N}\sum_j \Psi_{\theta'_j}(x)\right) - \frac{1}{N}\sum_j \Psi_{\theta'_j}(x)$$

where h(p)=-p log(p)-(1-p)log(1-p) defines the entropy of a distribution of complementary probabilities: p and 1-p. The above calculation requires calculating $\Psi_\theta(x)$ over the Monte Carlo samples, for each possible grating stimulus. Given a single sample, $\theta_j'$, that defines a CSF, $S_{\theta'_j}(f)$, the probability of a correct response for a grating of frequency, f, and contrast, c, is given by the psychometric function:

$$\Psi_\theta(f,c)=min(1-\epsilon,(1-0.5)*(1-10^{\beta \times [-S_\theta(f)-log_{10}(c)]}))$$

Use of this psychometric function assumes that the steepness parameter, β=2, does not change as a function of spatial frequency (Mayer & Tyler, 1986) and that the observers makes stimulus-independent judgments (lapses) on a small proportion of trials, ε=4%.

Response Collection and Bayesian Update

During the course of the experiment, the method applies Bayes rule to reiteratively update $p(\theta)$, given the response to that trial's grating stimulus. For the Bayesian update that follows each trial's outcome, we use the explicit gridded priors, rather than its samples. This calculation is computationally intensive, but its impact is mitigated by (1) only calculating the update for the actual stimulus and response on each trial, not for all potential stimuli; and (2) the increases in computing power expected with each generation of personal computers. As prescribed by Konstevich and Tyler (1999), to calculate the probability of the observed response (either correct or incorrect) to the stimulus s:

$$p(r_{correct}, s) = \Psi(s)$$

or $$p(r_{incorrect}, s) = 1 - \Psi(s)$$

the prior, $p_t(\theta)$, is used to weigh the response rates defined across the parameter space, $T_\theta$:

$$p(r_t | s_t) = \sum_\theta p(r_t, s_t) p_t(\theta)$$

This normalization factor, sometimes called the probability of the data, is used to update the prior, $p_t(\theta)$, to the posterior $p_{t+1}(\theta)$, via Bayes Rule:

$$p_{t+1}(\theta) = \frac{p_t(\theta) p(r_t, s_t)}{p(r_t | s_t)} \quad (18)$$

For estimating the four CSF parameters, the marginal means were calculated. The qCSF estimate is the CSF defined by the mean parameter vector theta.

Re-Iteration and Stop Rules

After the observer finishes trial t+1, the updated posterior is used as the prior for trial t+2. For a stopping criterion, the current qCSF application uses a fixed trial number. Other stopping criteria can also be implemented.

Example IV

Rapid Estimation of the Spatiotemporal Contrast Sensitivity Surface

Purpose. The spatiotemporal contrast sensitivity surface (CSS) describes visual sensitivity (1/threshold) to moving or flickering gratings as a function of spatial and temporal frequency (1). The CSS provides a fundamental characterization of the visual system in both normal and clinical populations. Many neuro-ocular diseases exhibit characteristic frequency-specific deficits on the CSS (2). To overcome the long testing times typical needed to measure the CSS, we develop a family of adaptive methods for its rapid estimation.

Method. The CSS is typically studied in orthogonal and diagonal slices through its surface: spatial contrast sensitivity functions (CSFs) at fixed temporal frequencies, temporal CSFs at fixed spatial frequencies, or constant-speed CSFs at co-varied spatial and temporal frequencies. We estimated these contrast sensitivity slices by combining Bayesian adaptive inference with a trial-to-trial information-gain strategy (3). To estimate the entire CSS, our novel procedure combined the information gained from adaptive runs dedicated to individual slices. Before each trial, the procedure evaluated expected gain within individual slices (6 spatial, 6 temporal, and 7 speeds) and selected a stimulus maximizing the information gain expected among all the slices. The final CSS estimate combined the surface estimates from all slices. In psychophysical experiments, we measured human sensitivity for motion direction discrimination over a large range of spatial (0.5-8 cycles/deg) and temporal frequencies (0.25-24 Hz).

Results. Simulation and psychophysical results suggest accurate CSS estimates are possible within 300-500 trials (15-25 minutes) with an average precision of 2-3 dB. Monte Carlo sampling of posteriors provides confidence regions for the CSS based on single adaptive runs.

Conclusion. This procedure offers a useful tool for clinical and practical applications that require a rapid but comprehensive evaluation of visual sensitivity.

What is claimed is:

1. A quick contrast sensitivity function (qCSF) method, comprising:
   (a) providing a prior probability density, $p(\theta)$, wherein said prior probability density reflects a current estimate of an observer's contrast sensitivity function;
   (b) selecting a grating stimulus, s, that minimizes the expected entropy of the Bayesian posterior;
   (c) displaying grating stimulus s to a subject;
   (d) receiving a response to s from the subject;
   (e) updating the prior probability density, $p(\theta)$ according to the Bayes rule and the response received in step (d);
   (f) reiterating steps (b) through (e); and
   (g) terminating the reiterating steps (b) through (e) according to a stopping criterion.

2. The method of claim 1, wherein $p(\theta)$ is defined over (1) peak sensitivity, $\gamma_{max}$, (2) peak spatial frequency, $f_{max}$, (3) bandwidth at half-peak sensitivity, $\beta$, and (4) low spatial frequency truncation, $\delta$.

3. The method of claim 1, wherein grating stimulus s is defined by spatial frequency and contrast.

4. The method of claim 1, wherein the stopping criterion is a predetermined number of trials.

5. The method of claim 1, further comprising determining whether a visual sensitivity of the subject is abnormal.

6. A device for visual examination, comprising:
   computation means for providing a prior probability density, $p(\theta)$, selecting a grating stimulus, s, that minimizes the expected entropy of the Bayesian posterior, updating the prior probability density, $p(\theta)$ according to the Bayes rule and a response to grating stimulus s by a subject to which grating stimulus s is displayed, and terminating a visual examination according to a stopping criterion, wherein said prior probability density reflects a current estimate an observer's contrast sensitivity function;
   display means coupled to the computation means for receiving grating stimulus s from the computation means and displaying grating stimulus s to the subject; and
   recording means for receiving the response to grating stimulus s by the subject and transmitting it to the computation means.

7. The device of claim 6, wherein $p(\theta)$ is defined over (1) peak sensitivity, $\gamma_{max}$, (2) peak spatial frequency, $f_{max}$, (3) bandwidth at half-peak sensitivity, $\beta$, and (4) low spatial frequency truncation, $\delta$.

8. The device of claim 6, wherein grating stimulus s is defined by spatial frequency and contrast.

9. The device of claim 6, wherein the stopping criterion is a predetermined number of trials.

10. The device of claim 6, further comprising diagnostic means for determining whether a visual sensitivity of the subject is abnormal.

11. A method for classifying contrast sensitivity functions (CSFs), comprising:
    (a) providing a prior probability of class membership, wherein the class membership is defined based on historical measurement of normal and abnormal contrast sensitivity functions;

(b) selecting a grating stimulus, s, that minimizes the expected entropy of the Bayesian posterior;
(c) displaying grating stimulus s to a subject;
(d) receiving a response to grating stimulus s from the subject;
(e) updating the prior probability of class membership according to the Bayes rule and the response received in step (d);
(f) reiterating steps (b) through (e); and
(g) terminating the reiterating steps (b) through (e) according to a stopping criterion.

12. The method of claim 11, wherein grating stimulus s is defined by spatial frequency and contrast.

13. The method of claim 11, wherein the stopping criterion is a predetermined number of trials.

14. The method of claim 11, further comprising determining the pathologic class of the subject if a visual sensitivity of the subject is abnormal.

15. A device for visual examination, comprising:
computation means for providing a prior probability of class membership, selecting a grating stimulus, s, that minimizes the expected entropy of the Bayesian posterior, updating the prior probability of class membership according to the Bayes rule and a response to grating stimulus s by a subject to which grating stimulus s is displayed, and terminating a visual examination according to a stopping criterion, wherein the class membership is defined based on historical measurement of normal and abnormal contrast sensitivity functions;
display means coupled to the computation means for receiving grating stimulus s from the computation means and displaying grating stimulus s to the subject; and
recording means for receiving the response to grating stimulus s by the subject and transmitting it to the computation means.

16. The device of claim 15, wherein grating stimulus s is defined by spatial frequency and contrast.

17. The device of claim 15, wherein the stopping criterion is a predetermined number of trials.

18. The device of claim 15, further comprising diagnostic means for determining the pathologic class of the subject if a visual sensitivity of the subject is abnormal.

19. A method for rapid measurement of spatiotemporal contrast sensitivity surface (CSS), comprising:
(a) providing prior spatial contrast sensitivity functions (CSFs) at predetermined temporal frequencies, temporal CSFs at predetermined spatial frequencies, and CSFs at spatial and temporal frequencies that co-vary to determine pre-specified constant speeds;
(b) selecting a grating stimulus, s, that maximizes the expected information gain from the Bayesian posteriors;
(c) displaying grating stimulus s to a subject;
(d) receiving a response to grating stimulus s from the subject;
(e) updating the prior CSFs according to the Bayes rule and the response received in step (d);
(f) reiterating steps (b) through (e); and
(g) terminating the reiterating steps (b) through (e) according to a stopping criterion.

20. The method of claim 19, wherein grating stimulus s is defined by spatial and temporal frequencies and contrast.

21. The method of claim 19, wherein the stopping criterion is a predetermined number of trials.

22. The method of claim 19, further comprising determining whether a visual sensitivity of the subject is abnormal.

23. A device for visual examination, comprising:
computation means for providing prior spatial contrast sensitivity functions (CSFs) at predetermined temporal frequencies, temporal CSFs at predetermined spatial frequencies, and CSFs at spatial and temporal frequencies that co-vary to determine pre-specified constant speeds, selecting a grating stimulus, s, that maximizes the expected information gain from the Bayesian posteriors, updating the prior CSFs according to the Bayes rule and a response to grating stimulus s by a subject to which grating stimulus s is displayed, and terminating a visual examination according to a stopping criterion;
display means coupled to the computation means for receiving grating stimulus s from the computation means and displaying grating stimulus s to the subject; and
recording means for receiving the response to grating stimulus s by the subject and transmitting it to the computation means.

24. The device of claim 23, wherein grating stimulus s is defined by spatial and temporal frequencies and contrast.

25. The device of claim 23, wherein the stopping criterion is a predetermined number of trials.

26. The device of claim 23, further comprising diagnostic means for determining whether a visual sensitivity of the subject is abnormal.

* * * * *